United States Patent
Wysocki et al.

(10) Patent No.: US 7,733,924 B2
(45) Date of Patent: Jun. 8, 2010

(54) PIEZO ACTIVATED MODE TRACKING SYSTEM FOR WIDELY TUNABLE MODE-HOP-FREE EXTERNAL CAVITY MID-IR SEMICONDUCTOR LASERS

(75) Inventors: Gerard Wysocki, Houston, TX (US);
Frank K. Tittel, Houston, TX (US);
Robert F. Curl, Houston, TX (US)

(73) Assignee: William Marsh Rice University, Houston, TX (US)

(*) Notice: Subject to any disclaimer, the term of this patent is extended or adjusted under 35 U.S.C. 154(b) by 0 days.

(21) Appl. No.: 11/203,785

(22) Filed: Aug. 15, 2005

(65) Prior Publication Data
US 2007/0047599 A1    Mar. 1, 2007

(51) Int. Cl.
*H01S 3/10* (2006.01)
(52) U.S. Cl. ......................... 372/20
(58) Field of Classification Search ............ 372/20, 372/102
See application file for complete search history.

(56) References Cited

U.S. PATENT DOCUMENTS

| | | | |
|---|---|---|---|
| 6,560,259 B1* | 5/2003 | Hwang | 372/45.01 |
| 6,704,332 B2* | 3/2004 | Chapman et al. | 372/20 |
| 2003/0231691 A1* | 12/2003 | Marron | 372/97 |
| 2005/0105566 A1* | 5/2005 | Sacher | 372/20 |
| 2005/0243875 A1* | 11/2005 | Le et al. | 372/20 |

OTHER PUBLICATIONS

Maulini, Richard, et al., "Continuous-wave operation of a broadly tunable thermoelectrically cooled external cavity quantum-cascade laser," Optics Letters, vol. 30, No. 19 (Oct. 1, 2005), Optical Society of America, pp. 2584-2586.

Namjou, K., et al., "Sensitive absorption spectroscopy with a room-temperature distributed-feedback quantum-cascade laser," Optics Letters, vol. 23, No. 3 (Feb. 1, 1998), Optical Society of America, pp. 219-221.

Wysocki, G., et al., "Widely tunable mode-hop free external cavity quantum cascade laser for high resolution spectroscopic applications," Applied Physics B: Lasers and Optics, vol. 81 (2005), pp. 769-777.

(Continued)

*Primary Examiner*—Minsun Harvey
*Assistant Examiner*—Patrick Stafford
(74) *Attorney, Agent, or Firm*—Conley Rose, P.C.; Rodney B. Carroll

(57) ABSTRACT

A widely tunable, mode-hop-free semiconductor laser operating in the mid-IR comprises a QCL laser chip having an effective QCL cavity length, a diffraction grating defining a grating angle and an external cavity length with respect to said chip, and means for controlling the QCL cavity length, the external cavity length, and the grating angle. The laser of claim 1 wherein said chip may be tuned over a range of frequencies even in the absence of an anti-reflective coating. The diffraction grating is controllably pivotable and translatable relative to said chip and the effective QCL cavity length can be adjusted by varying the injection current to the chip. The laser can be used for high resolution spectroscopic applications and multi species trace-gas detection. Mode-hopping is avoided by controlling the effective QCL cavity length, the external cavity length, and the grating angle so as to replicate a virtual pivot point.

19 Claims, 10 Drawing Sheets

OTHER PUBLICATIONS

Patent application entitled "Fast wavelength tuning techniques for external cavity lasers," by Gerard Wysocki, et al., filed Jan. 7, 2009 as U.S. Appl. No. 12/349,839.

Provisional patent application entitled "Fast wavelength tuning technique for external cavity lasers," by Gerard Wysocki, et al., filed Jan. 10, 2008 as U.S. Appl. No. 61/020,334.

* cited by examiner

PIEZO ACTIVATED MODE TRACKING SYSTEM FOR WIDELY TUNABLE MODE-HOP-FREE EXTERNAL CAVITY MID-IR SEMICONDUCTOR LASERS

STATEMENT REGARDING FEDERALLY SPONSORED RESEARCH OR DEVELOPMENT

This invention was made with government support under Grant No. NAG9-01482 awarded by NASA-JSC and under Grant No. DE-AC05-76R01830—contract 14813 awarded by Pacific Northwest National Laboratory (PNNL), Richland, Wash. The United States government has rights in the invention.

CROSS-REFERENCE TO RELATED APPLICATIONS

Not Applicable.

FIELD OF THE INVENTION

The present invention relates generally to laser spectroscopy and more specifically to a widely tunable, mode-hop-free semiconductor laser operating in the mid-infrared range.

BACKGROUND OF THE INVENTION

Infrared laser absorption spectroscopy is an extremely effective tool for detecting trace gases. Presently, however, the usefulness of laser spectroscopy is limited by the lack of broadly tunable, mode-hop-free sources in the spectroscopically important mid-IR region, defined herein as wavelengths between ~3 and 30 μm.

Quantum cascade (QC) and Interband Cascade (IC) lasers are excellent light sources for spectroscopic applications in the mid-IR. The high power of QC and IC lasers permits the use of advanced detection techniques that improve S/N ratio of trace gas spectra and decrease the apparatus size. In addition, the large wavelength coverage available with QC and IC lasers allows numerous molecular trace gas species to be monitored.

Spectroscopic applications require single mode operation, which can be achieved by introducing a distributed feedback (DFB) structure into the QCL active region. Experiments using distributed feedback (QC-DFB) lasers have demonstrated the efficacy of these devices for sensitive, highly selective real time trace gas concentration measurements based on absorption spectroscopy, with sensitivities of several parts per billion (See e.g. K. Namjou et al., "Sensitive absorption spectroscopy with a room-temperature distributed-feedback quantum-cascade laser," Optics Letters, V. 23, n. 3, Feb. 1, 1998, which is hereby incorporated by reference).

Although QC-DFB lasers show high performance and reliability, they are useful only over narrow wavelength ranges. This is because the range of wavelength tuning of the emitted laser radiation is limited by the tuning range of the DFB structures. Typically the maximum tuning range of DFB-QCLs is of ~10 $cm^{-1}$ and is achieved by varying either the temperature of the chip or the laser injection current. One of the disadvantages of thermal tuning is that it affects the effective gain of the QCL, which in turn causes the output laser power to decrease with increasing temperature of the QCL chip.

Thus, to take full advantage of the wavelength tunability potential of a QCL, an external cavity (EC) configuration must be applied. However, high quality AR coatings, which are necessary for mode-hop-free EC laser operation are not available for the mid-IR spectrum. The lack of effective anti-reflective coatings in the mid-IR range means that it is impossible to achieve tuning across the wavelengths within the gain curve without experiencing mode-hopping. When mode-hopping occurs, the laser changes its frequency discontinuously. A laser that exhibits discontinuous tuning is not useful in high resolution spectroscopic applications such as spectral measurements of ro-vibrational molecular transitions.

One known approach to avoiding mode-hopping is to change the external cavity length synchronously with the grating angle, which is usually realized by appropriate selection of the grating pivot point. This approach works when an effective AR coating is available, such as in the visible and near-IR spectral regions, but cannot be used in the absence of an effective AR coating, such as in the mid-IR range.

Hence, it is desirable to provide a widely tunable, mode-hop-free external cavity laser that is functional in the mid-IR wavelengths.

SUMMARY OF THE INVENTION

The present invention features a QC laser spectrometer that is suitable for high resolution spectroscopic applications and multi-species trace-gas detection in the mid-IR. Through the implementation of a novel EC-QCL architecture, the present device avoids the shortcomings of prior devices and provides a wide tunability and mode-hop-free frequency scanning of the external cavity laser that is functional for mid-IR wavelengths. The instrument employs a piezo-activated cavity mode tracking system for mode-hop free operation. The mode-tracking system provides independent control of the EC length and diffraction grating angle. The flexibility of this arrangement allows the instrument to be used with other lasers at other wavelengths without changing the EC configuration. In addition, the QC and IC gain chips can be used with current AR coating technology and are functional even in the absence of any AR coating on the output laser facet.

In some embodiments, a mid-IR laser constructed in accordance with the present invention will comprise a laser chip defining an internal cavity and having an effective QCL cavity length, a diffraction grating defining a grating angle and an external cavity length with respect to said chip, means for controlling the QCL cavity length, means for controlling the external cavity length, and means for controlling the grating angle. The chip preferably emits light having wavelengths in the range of 3-30 μm. The chip may include no anti-reflective coating, or may include an anti-reflective coating that has a reflectance greater than 0.5%. The diffraction grating is preferably mounted on a platform that is pivotable and translatable relative to said chip and the QCL cavity length can be varied by varying the injection current to the chip. Such a device is well-suited for high resolution spectroscopic applications and multi species trace-gas detection.

In other embodiments, a method for operating a mid-IR laser so as to avoid mode-hopping comprises a) providing a laser chip that defines an internal cavity and has an effective QCL cavity length, b) providing a diffraction grating that defines a grating angle and an external cavity length with respect to said chip, c) providing power to said chip so that it amplifies electromagnetic radiation within defined gain curve comprising a range of wavelengths, and d) tuning the chip while controlling the effective QCL cavity length, controlling the external cavity length, and controlling the grating angle so that the laser frequency can be tuned through wavelengths under the gain curve without mode-hopping.

Thus, the present invention comprises a combination of features and advantages that enable it to overcome various problems of prior devices. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENTS

System

Figure 1:
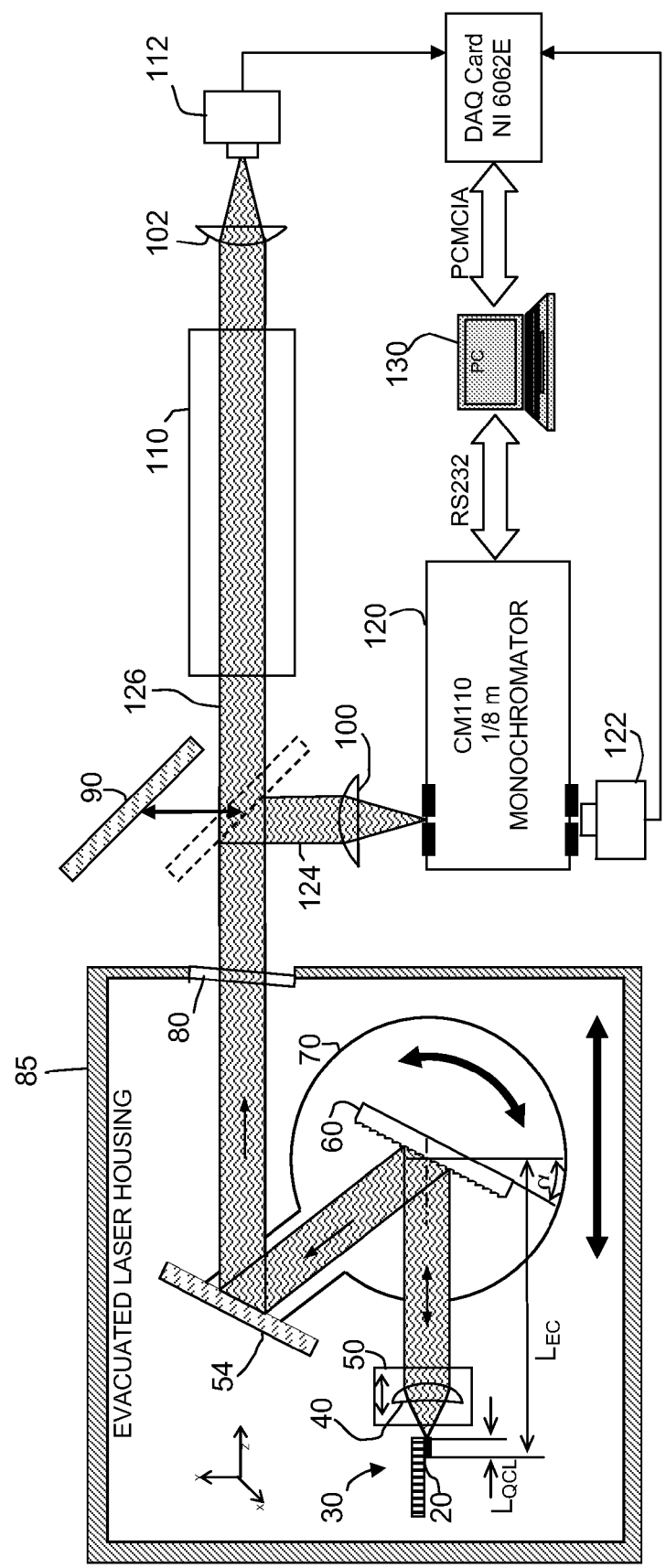
FIG. 1 is a schematic diagram showing an external cavity quantum cascade laser (EC QCL) constructed in accordance with a preferred embodiment of the invention.

Referring initially to FIG. 1, a preferred embodiment of a system 10 incorporating the principles of the present invention may include a quantum cascade laser 20, a thermoelectric cooler 30, a collimating lens 40, a motorized 3D translation stage 50, a diffraction grating 60, a mirror 54, a movable platform 70 (sometimes referred to herein as a "rotary stage"), a window 80, a movable mirror 90, lenses 100, 102, a reference cell 110, a first photodetector 112, a monochromator 120, a second photodetector 122, and a microprocessor 130 with data acquisition electronics coupled to the first and second photodetectors 112, 122. While the system illustrated in FIG. 1 does not include a sample cell, one skilled in the art will recognize that either reference cell 110 or monochromator 120 may be replaced with a sample cell. Alternatively, an additional "arm" of the laser path could be formed using a beam splitter or mirror, and used for sample measurement.

Laser 20 preferably includes QCL chip 22 such as a QC Fabry-Perot device fabricated using bound-to-continuum design, which significantly improves the available laser bandwidth. Preferred chips have a tuning range that is more than 10% of their center wavelength (e.g 0.5 µm tunability at 5 µm).

As is known in the art, a thermoelectric cooler 30 will typically be associated with chip 22 in order to maintain a constant temperature of the chip 22. Collimating lens 40 is preferably a fast (f-number f#≦1) aspheric lens with AR-coating, corrected to eliminate spherical aberrations, designed especially for calibration of the highly divergent beams. By way of example only, collimating lens 40 may be a 1" diameter, f/0.6, Ge, AR-coated lens designed for wavelengths between 3 and 12 µm. In the embodiment shown, collimating lens 40 is mounted on translation stage 50. Stage 50 is preferably a conventional 3D translation stage such as are known in the art for providing linear motion. Stage 50 is preferably equipped with remotely controlled piezo-motors and is used for positioning lens 40 as needed for laser optical alignment. In the embodiment illustrated in FIG. 1, the system is sealed within a vacuum-tight housing 85, so the simplest way to align lens 40 is with movable stage 50. In embodiments where lens 40 is not inside a housing, other modes of adjustment, including manual adjustment, may be used. In most instances, alignment of lens 40 is performed once after positioning chip 22 and additional movement of lens 40 is not required during operation and frequency scanning of the laser.

Diffraction grating 60 may be any suitable reflective grating that has appropriate resolving power and efficiency, including but not limited to ruled reflective diffraction gratings blazed for the desired wavelength region. An example of a suitable grating is a ruled diffraction grating blazed for a wavelength of 5.4 µm having 150 grooves/mm. Likewise, mirror 65 may comprise any suitable reflecting surface, including but not limited to gold, silver or aluminum coated mirrors, which can provide high reflectivity within broad range of wavelengths. Diffraction grating 60 and a mirror 65 are preferably both mounted on platform 70. Alternatively, grating 60 and mirror 65 can be mounted separately but mechanically linked so as to achieve the desired relative positioning, as discussed below.

Movable platform 70 allows independent control of both the external cavity length and grating angle. In preferred embodiments, the platform position is controlled by both a piezo-actuated linear translation stage and a rotary stage, such as may be purchased commercially. The rotary stage is equipped with a motorized coarse angle control and piezo-actuated fine control. These two controls allow precise positioning of the EC length and grating angle. In each of the stages, translation and rotation, a PZT is connected at one end to the base of the device or another fixed component and at its other end to the moving part of the stage. In the linear stage, the PZT is preferably used instead of a standard micrometric screw. In contrast, in the rotary stage a linear motor is preferably connected to the base and the PZT is connected to the moving part and the motor and the PZT press against each other at their tips. This allows both coarse and fine movement of the rotary stage. Mirror 65, which is mounted on the same platform, ensures a constant direction for the output EC-QCL beam.

Window 80 may be constructed of any suitable material that has good transmission at the desired wavelength(s), such as ZnSe, KBr, and $CaF_2$ or the like. In some embodiments, window 80 comprises $CaF_2$ with a thickness of 2-6 mm. Window 80 is preferably tilted with respect to the light beam passing through it so that back reflection (Fresnel reflection) of the light from the window surfaces to the laser cavity can be avoided. When mounted perpendicular to the laser beam the window 80 is preferably AR-coated to avoid back-reflection. In the embodiment shown, the whole EC system is placed inside a vacuum-tight housing and laser light exits the housing through window 80. In other embodiments, only the laser chip will be inside the housing, the collimating lens will act as an output window for the laser light and the grating with all the manipulators will be outside.

Like mirror 65, mirror 90 can be any suitable reflecting or partial reflecting, partially transmitting device such as are known to those skilled in the art. Lenses 100, 102 can comprise any material suitable for transmission of the wavelength of the laser light and may be configured to have any desired optical properties. In a preferred embodiment, lenses 100, 102 are ZnSe lenses with 1" focal lengths.

Reference cell 110, photodetectors 112, 122, and monochromator 120 may all be commercial or custom components as will be understood by those skilled in the art. An example of a suitable photodetector is a Hg—Cd—Zn—Te, TE-cooled detector, available from Vigo Systems under type PDI-2TE-6.

The complete spectrometer depicted in FIG. 1 provides two laser beam paths 124, 126, which can be selected by introducing movable mirror 90 into the optical axis, or not, respectively. In preferred embodiments, optical arm 124 includes a ⅛ wavelength monochromator for coarse wavelength measurements. The other arm 126 may be used for spectroscopic absorption measurements including relative and absolute spectral frequency standards such as a gas reference absorption cell or an air spaced etalon. As mentioned above, either beam path 124, 126 may be passed through a sample cell (not shown), or a portion of the beam may be split and used for sample measurements.

Operation

Figure 2:
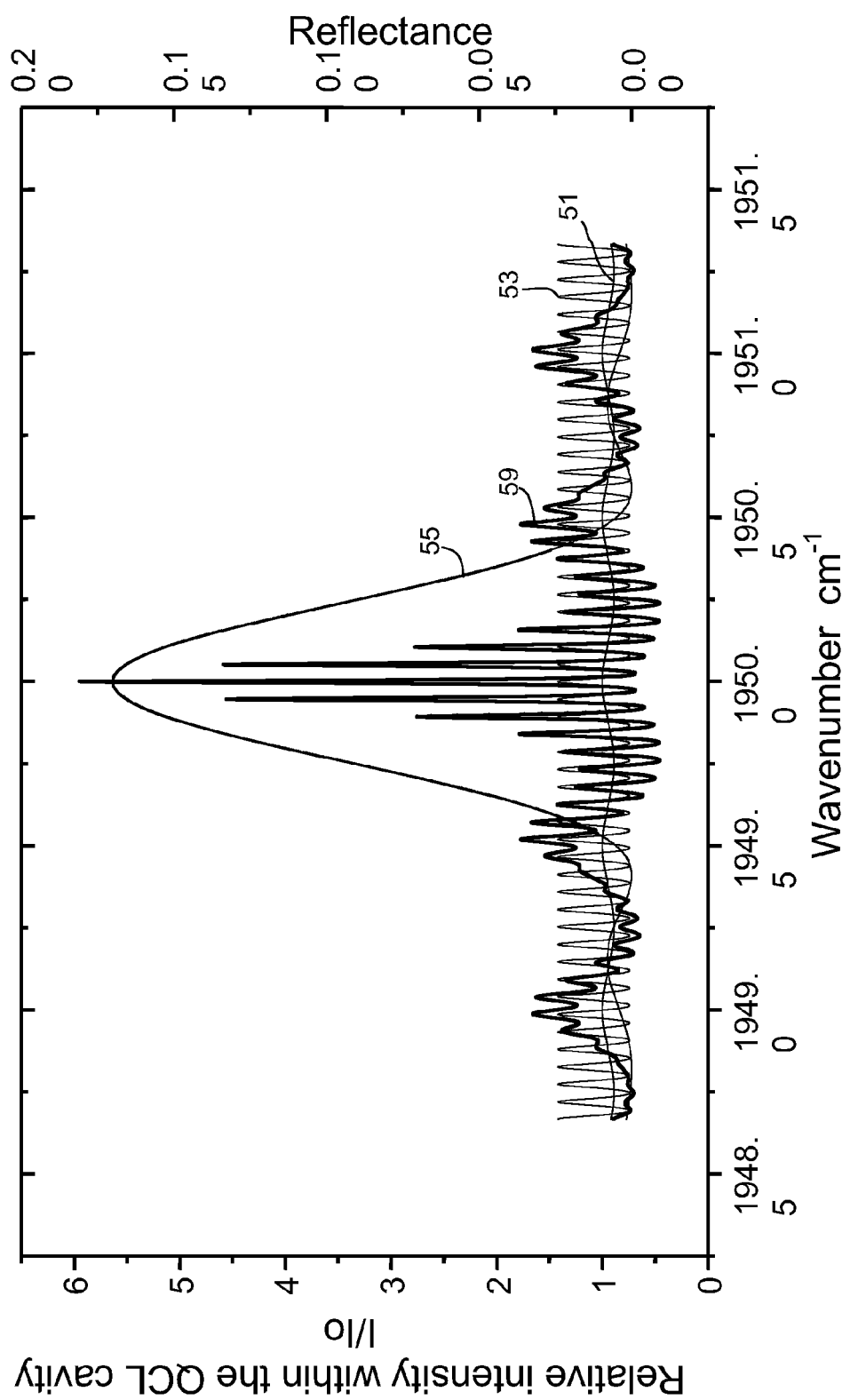
FIG. 2 is a plot illustrating the convergence of modeled spectral characteristics of three types of wavelength selective elements present in the system as carried out in accordance with the present invention.

In operation, power is supplied to chip 22, causing it to emit light. The wavelength range for which laser amplification can be achieved, referred to as the gain curve of the chip, are determined by the construction of the chip. Details of QCL chip construction are known to those skilled in the art and are beyond the scope of the present disclosure. FIG. 2 shows a numerical simulation of the relative changes in the optical intensity between back and front facets of the QCL as a function of optical frequency for three components of a hypothetical EC-QCL coupled cavity system configured as in FIG. 1, calculated with an assumption of transparent QCL medium (G=L) and with each frequency tuning element centered at the same wavelength. The figure depicts three types of spectral characteristics of wavelength selective elements in an EC QCL system lacking an effective AR coating on the chip exit facet. Specifically, plot 51 illustrates the relative intracavity intensity variation attributable to the lack of effective AR coating. Plot 53 illustrates the relative intracavity intensity variation attributable to the EC length, and plot 55 illustrates the variation of grating reflectance as a function of optical frequency. In FIG. 2, the system has been simulated such that all three frequency tuning elements are centered at the same wavelength. Plot 59 illustrates the composite function resulting from plots 51, 53, and 55.

Figure 3:
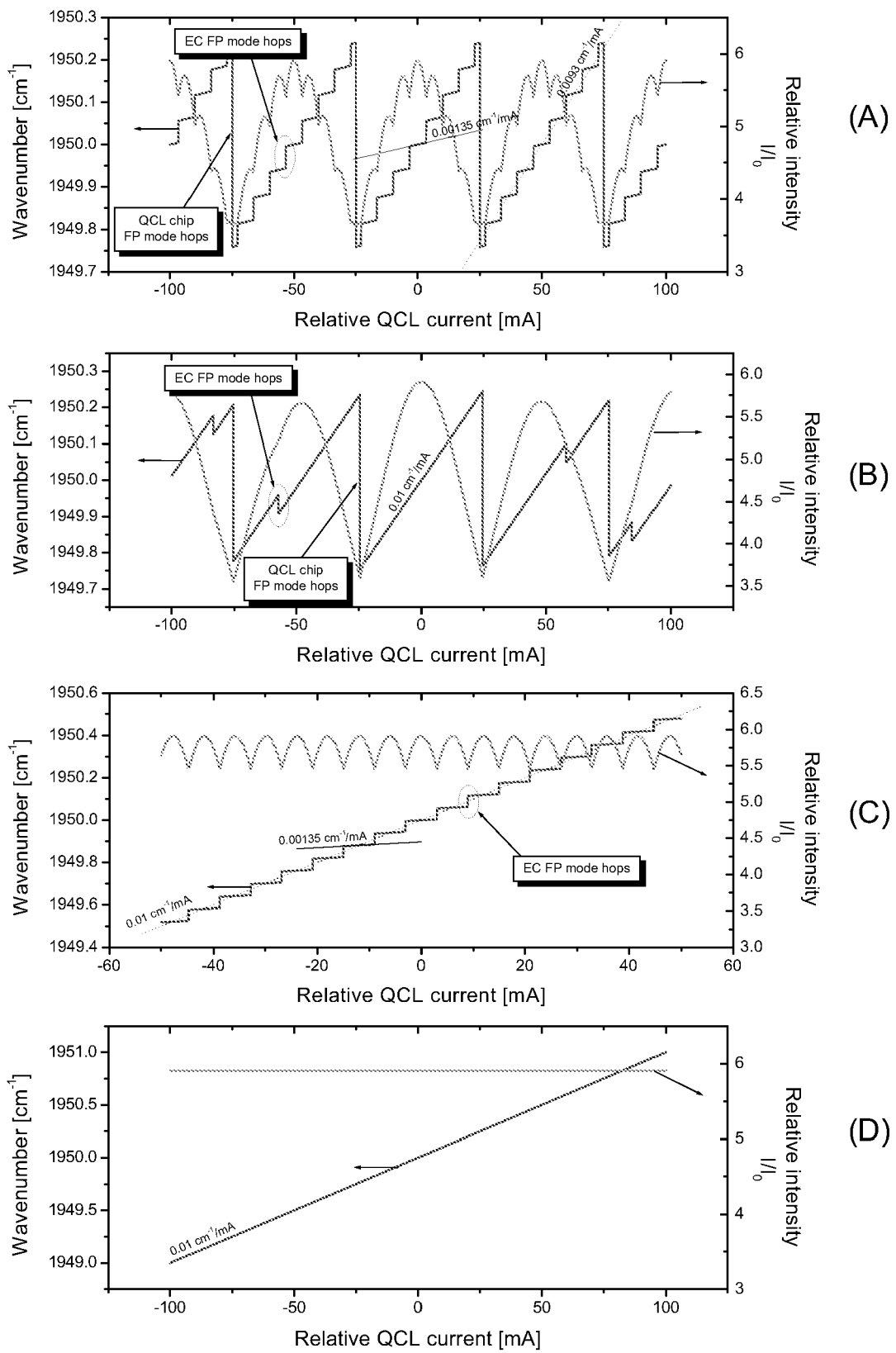
FIGS. 3A-D are plots illustrating a simulation of various functional aspects of the present device.

Referring now to FIG. 3, plots A-C illustrate results of the QCL FP resonator length scan simulation showing an optical frequency of the strongest longitudinal mode and its relative intensity as a function of a relative QCL current. Plot 3A shows the effect of tuning of the QCL current without applying any mode tracking on intracavity optical intensity; plot 3B shows the effect of tuning of the QCL current with simultaneous tracking of the EC length only on intracavity optical intensity; and plot 3C shows the effect of tuning of the QCL current with simultaneous tracking of the grating angle only on intracavity optical intensity. Plot 3D illustrates complete mode tracking with concurrent use of all tuning elements. The x scale in plots A, B, C and D shows detuning from the state depicted in FIG. 2, which is expressed as a relative QCL current change calculated using experimentally measured coefficients From plots 3A and 3B, it can be seen that the lack of effective AR coatings in the mid-IR range causes mode-hopping associated with the presence of the internal cavity. More effective coatings would reduce the resulting power fluctuations and mode-hopping related to presence of the internal cavity. In the absence of a perfect coating, the effects caused by the presence of internal cavity can be addressed only by applying an appropriate frequency tuning methodology.

Thus, until effective AR coatings in the mid-IR range are available, mid-IR lasers have a seemingly intractable problem of mode-hopping, which is eliminated with the system and method of the present invention. In preferred embodiments of the present invention, mode-hopping is eliminated by changing the refractive index of the material while simultaneously tuning both the external cavity length and the grating angle. Modulation of refractive index of material is accomplished by the modulation of the injection current to the chip. Complete mode tracking allows mode-hop-free frequency tuning over the entire range, as illustrated in plot 3D. No modulation of intra-cavity intensity is observed, which corresponds to a stable optical power of the active laser.

Experimental

To confirm the principles disclosed herein, a laser corresponding to the schematic illustration of FIG. 1 was built. The preferred components indicated above were used and the translation and rotation stages were a Physik Instrumente model: M-014.00 with a piezo actuator model: P-840.60 and a Physik Instrumente model: M-035.DP1, respectively.

The gain chip used in the experimental EC QCL was fabricated using a bound-to-continuum design using known technology and applying essentially the same processing methods and parameters described in R. Maulini, D. A. Yarekha, J. M. Bulliard, M. Giovannini, and J. Faist and E. Gini, "Continuous-wave operation of a broadly tunable thermoelectrically-cooled external cavity quantum-cascade laser," accepted for publication to Optics Letters (April 2005) but the Principles of the invention can be applied to any laser system containing a QCL chip. A high-reflection (HR) coating ($Al_2O_3$/Au 300 nm/100 nm) was deposited on the back facet of the experimental chip. Although the present invention allows mode-hopping to be avoided even in complete absence of an AR coating, an anti-reflection (AR) coating ($\lambda$/4 thick $Al_2O_3$ layer) was deposited on the front facet of the experimental chip. For purposes of calculation, we estimated and assumed the AR coating reflectance to be 3%.

Due to various nonlinearities in the system, such as PZT hysteresis or laser saturation, the control voltages applied to the PZT mode tracking system are preferably set individually for each set of applied operating conditions.

Demonstration of Mode-Hop Free Wavelength Tracking

The performance of the mode tracking system was evaluated experimentally. The dependence of the laser frequency upon the position and angle of the diffraction grating controlled by the PZT actuators and the motor was measured separately for each actuator. All measured characteristics showed high linearity with the coefficients of: −0.0064 cm$^{-1}$/unit for the motorized grating angle tuning, 0.049 cm$^{-1}$/V (voltage applied to PZT actuator) for the PZT controlled grating angle tuning, and 0.036 cm$^{-1}$/V for the PZT controlled EC length tuning. In order to avoid certain factors such as PZT hysteresis, and translation stage mechanical backlash the wavelength scan is preferably optimized only in a single direction, which assures its good reproducibility and allows averaging of long scanning sequences.

Figure 4:
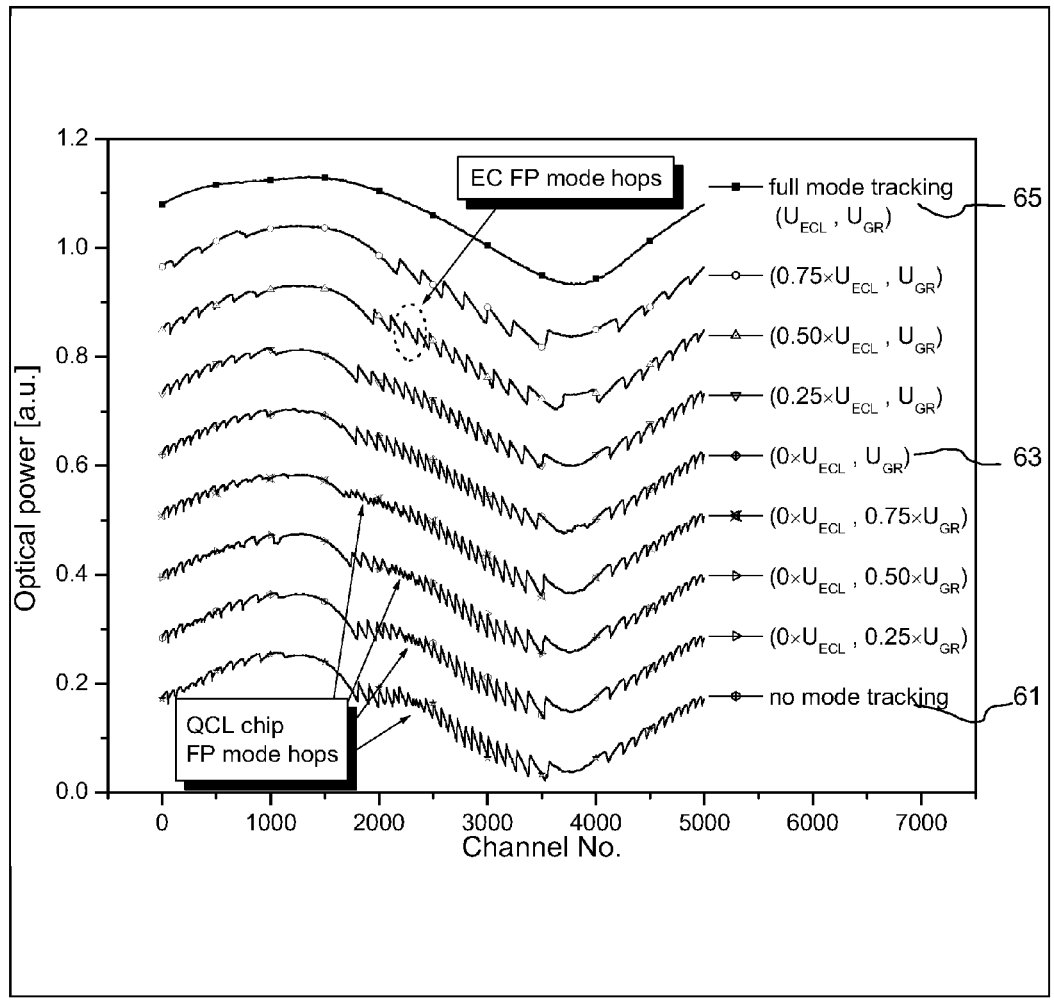
FIG. 4 is a plot illustrating the elimination of mode-hopping for a real quantum cascade laser in an external cavity configuration using a PZT-actuated cavity mode tracking system constructed in accordance with the present invention.

To demonstrate the efficiency of the mode tracking system, the output optical power of the EC-QCL was monitored during an operation while applying different fractions of control signals $U_{EC}$ and $U_{GR}$ (for the EC length and for the grating angle respectively) required for full mode tracking. The laser was driven by ~630 mA injection current and modulated with arbitrary sinusoidal waveform. The results of this experiment are presented in FIG. 4, which shows successive laser power time series recorded for different stages of the applied laser mode frequency tracking. By analogy to the simulation above (compare to FIG. 3) three of the discussed modes of operation can be observed with: no wavelength tracking (control signals $U_{EC}$ and $U_{GR}$ not applied), plot 61, only grating wavelength tracking (only $U_{GR}$ applied in full), plot 63, and full wavelength tracking (both $U_{EC}$ and $U_{GR}$ applied in full), plot 65. In each of the plots, the QCL current is modulated in the same way. As can be seen in FIG. 4, both QCL FP resonator mode hops and EC FP resonator mode hops are present when partial mode tracking is used. Increasing use of the PZT control signals results in progressive separation of the mode hops, and finally leads to complete laser longitudinal mode tracking and elimination of mode hops (plot 65).

Wavelength Tuning

Figure 5:
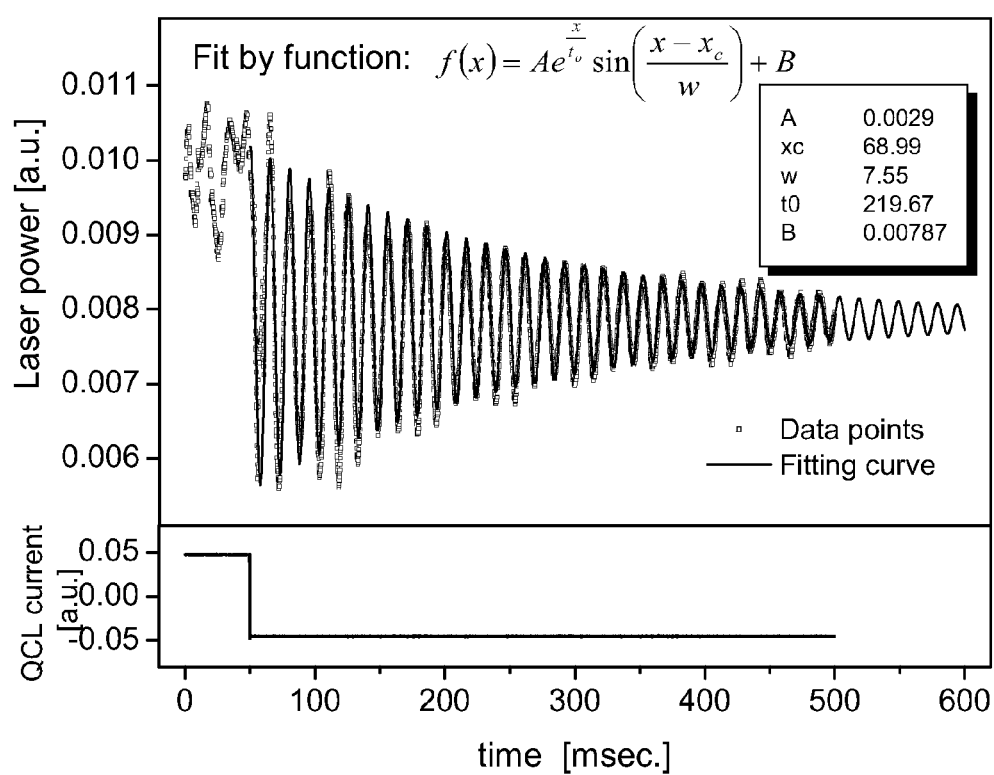
FIG. 5 is a plot illustrating the EC-QCL response of the same system as FIG. 4 measured with excitation by a step-like input signal.
Figure 6:
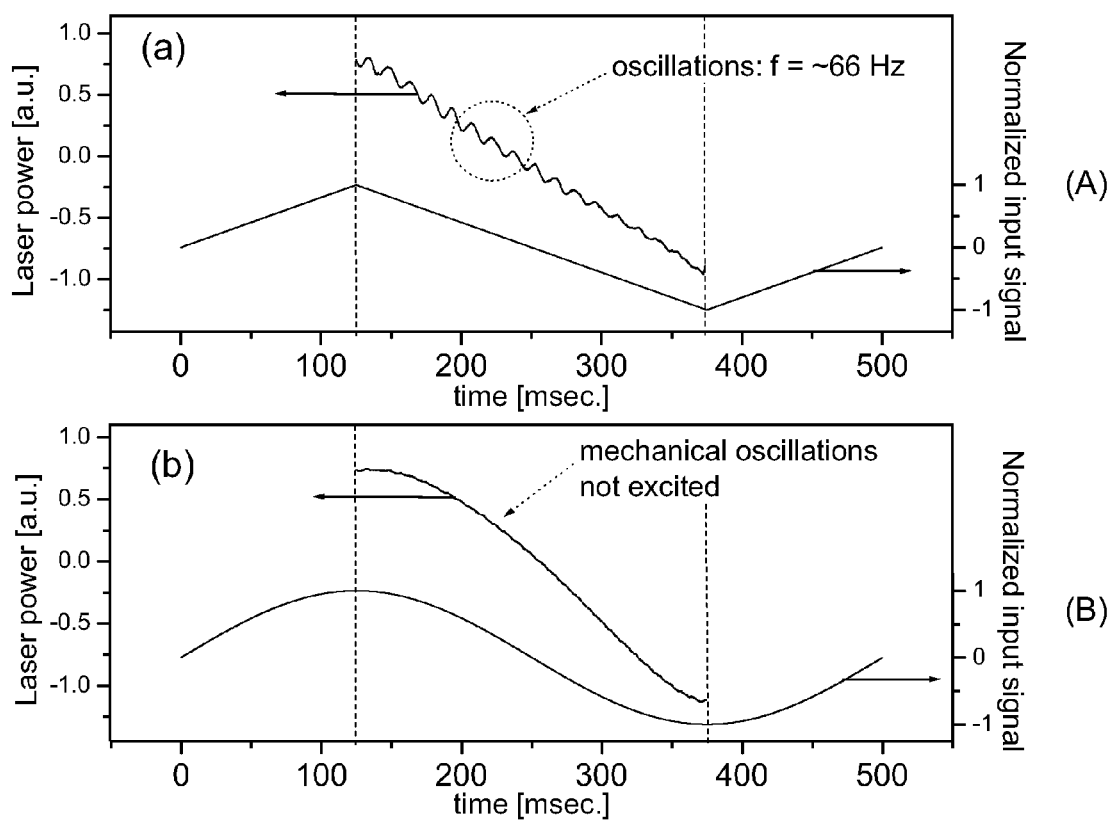
FIGS. 6A-B are plots illustrating the EC-QCL response of the same real system as FIG. 4, where the waveforms applied to modulate laser wavelength are A) a triangular waveform, and B) a sinusoidal waveform.

The wavelength tuning speeds in external cavity laser systems are typically limited by the mechanical properties of their architecture. Mechanical instability of the present system related to its vibrational resonances is likewise the main limiting factor for the performance of wavelength scanning. The wavelength scan in this system is controlled using a function generator, whose signal is used to modulate the QCL injection current and after appropriate conditioning of its amplitude and phase supplied as control signals to drive the PZT actuators of the EC-QCL. To determine the mechanical resonance frequency of the system, a rectangular waveform was applied to the input of the EC-QCL and the laser output was monitored. The response of the system is plotted in FIG. 4. Damped oscillations of the laser power are visible in the recorded photodetector signal as a result of mechanical vibrations excited in the EC laser system. The data points were fitted by a damped sinusoidal function and the frequency of these vibrations was measured to be $f_m \cong 66$ Hz with a characteristic decay time of ~220 msec. The reported prototype system consists only of commercially available components. The mass of the elements, which are a part of the EC manipulation system that must be actuated by the PZT, is relatively high and therefore such a low resonance frequency value was expected for this system. In order to suppress self-induced vibrations, the system should be driven by signals which do not excite any harmonics of the mechanical frequency. In this case, sinusoidal signals at frequencies lower than $f_m/10$ are expected to provide optimum operating conditions and good performance of the laser. The system responses recorded for both a conventional triangular waveform and a sinusoidal waveform scan, which is preferable for the present system, are illustrated in FIGS. 5A and 5B, respectively. The applied parameters: peak-to-peak amplitude of ~50 mA$_{p-p}$, and frequency of 2 Hz were the same for both waveforms. From FIG. 5 it can be seen that the triangular signal due to rapid changes of the scan direction (the Fourier transform of such a signal contains high frequency harmonics) causes excitation of the gradually fading mechanical vibrations, which are not induced during sinusoidal scanning. Therefore in all experiments performed with EC-QCL a sinusoidal wavelength modulation was applied.

Resolution

Theory predicts that the linewidth of a semiconductor laser can be reduced by extension of its cavity by a passive section. Thus, the external cavity of the present invention may also improve resolution of laser based spectrometers. For trace gas detection, resolutions of 0.001 cm$^{-1}$ or better, which corresponds to a typical (so called Doppler) linewidth of the molecular transition at reduced pressures, are considered high resolution. To achieve such a resolution, the laser must have a linewidth that is at least in this range or narrower than 0.001 cm$^{-1}$ (30 MHz). The present laser is estimated to have a resolution of less than 5 MHz based on the resolution of preliminary spectroscopic scans, as described below.

With the exemplary components, the system achieved a resolution of 0.9 nm and ±520 μrad for external cavity length and grating angle respectively. The coarse tuning by the linear motor can be performed within a range of ±6.3° with the actual position measured by a built-in encoder with a resolution of ~1.4 μrad/unit. The piezo-actuator controlling the external cavity length provides a total travel range of 90 μm±20%.

Spectroscopic Measurements

Figure 8:
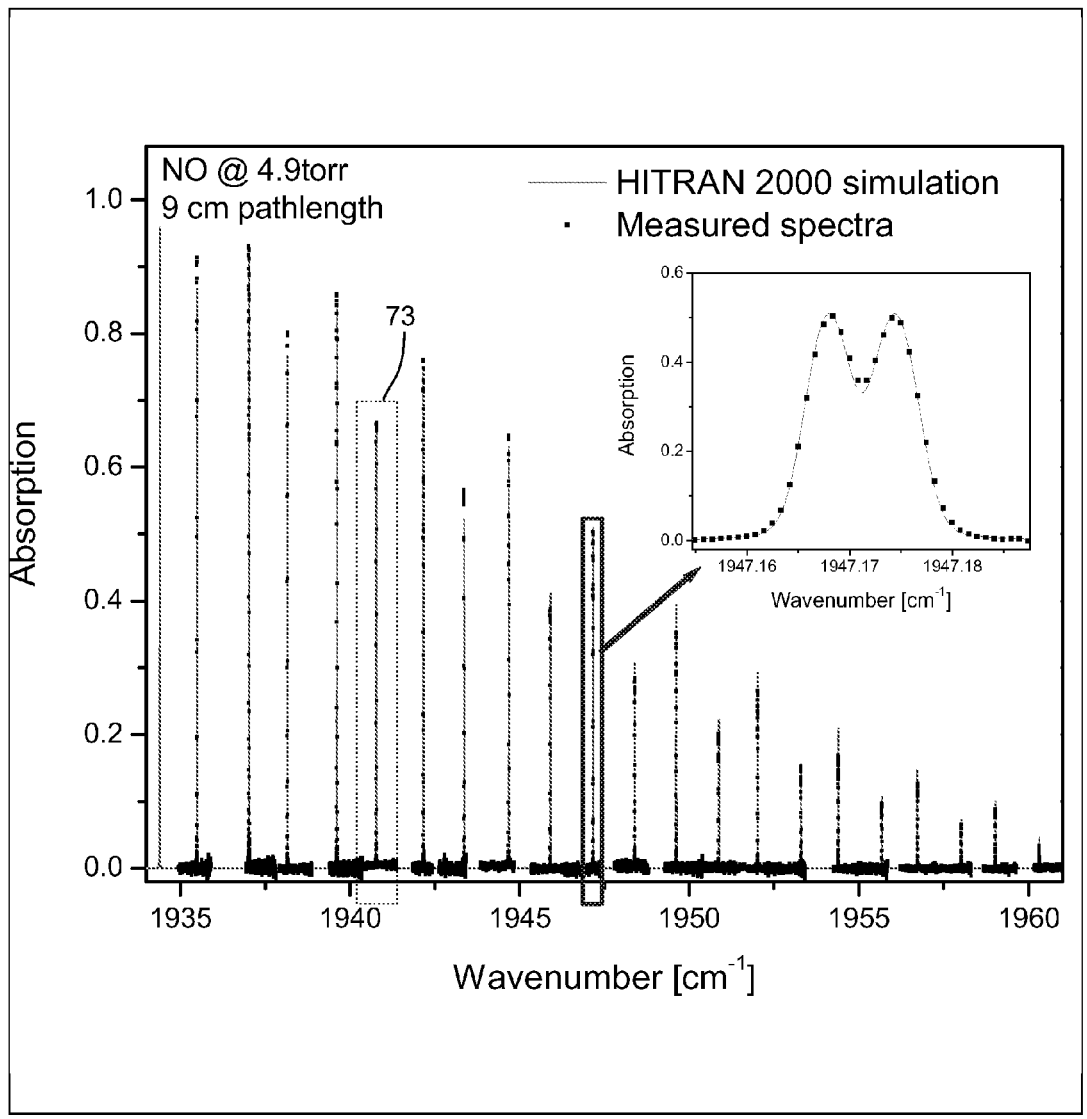
FIG. 8 are predicted and measured nitric oxide absorption spectra measured at different diffraction grating angles of the external cavity quantum cascade laser. The narrow laser linewidth allows precise resolution of two spectral peaks separated by ~0.006 cm-1 (see inset)
Figure 9:
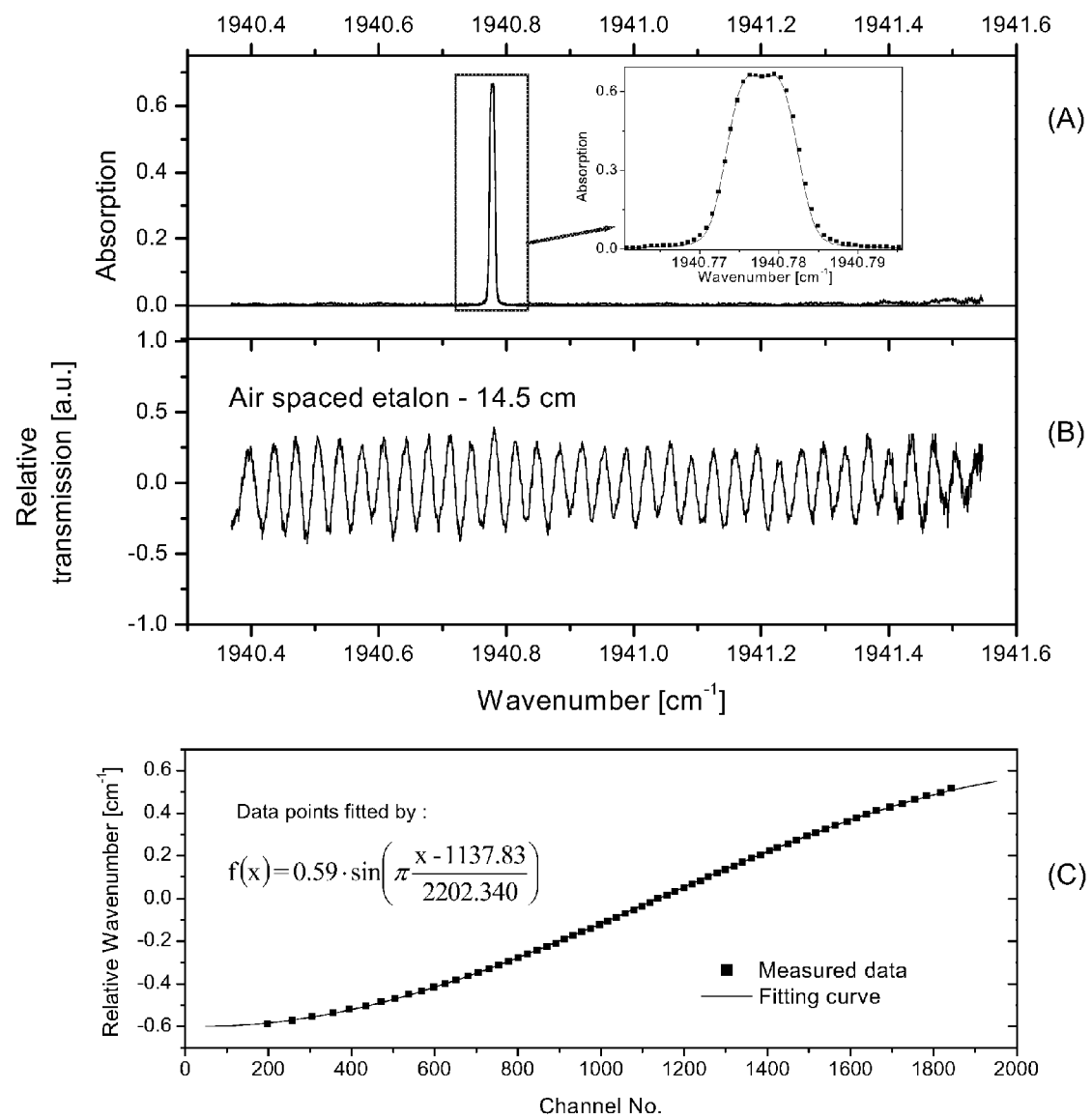
FIG. 9 is a plot of a NO-$R_{3/2}$ (20.5) spectrum recorded within a range of a single scan of the EC-QCL.

Spectroscopic absorption measurements of nitric oxide (NO) and water H$_2$O at reduced pressures were performed using the systems described above and demonstrated a wide wavelength tunability of the EC-QCL, along with its suitability for high resolution spectroscopy. The measured spectrum of a large section of the P-branch of the NO ro-vibrational spectrum between 1935 and 1961 cm$^{-1}$, which could be accessed by the present EC-QCL and a corresponding HITRAN 2000 simulation are shown in FIG. 8. The successive spectra were recorded for different positions of the diffraction grating angle. Each spectrum was calculated using the average of 10 single 5000-points scans within 5 sec. A single high resolution spectrum containing spectral absorption data in range of ≧1 cm$^{-1}$ can resolve spectral features separated by less than 0.006 cm$^{-1}$ (see the inset of FIG. 8 depicting the NO—R$_{1/2}$ (23.5) line). All scans were performed using sinusoidal modulation (~112 mA$_{p-p}$ at 2 Hz) of the laser current at an operating point of ~650 mA. For scan calibration an air-spaced low finesse etalon constructed of two ZnSe wedged windows separated by 14.5 cm was introduced into the beam path. A typical set of data recorded for a one of the component spectra presented in FIG. 8 is shown in FIG. 9. A wavelength calibrated spectra of NO—R$_{3/2}$ (20.5) (marked in FIG. 8 with phantom box 73), along with the associated etalon fringe pattern and the calculated calibration curve are presented in the plots of FIGS. 9A, B, and C, respectively. In this spectral region the separation of the component lines in NO R$_{3/2}$ doublets is much smaller than in the previously presented NO R$_{1/2}$ line. However, the fine spectral structure at the top of the line can still be resolved as shown in the inset of FIG. 9A.

A calibration was performed for each single spectrum separately. The shape of the calibration curve presented in 9C is typical for all measured spectra. A fit of the calibration curve by the sinusoidal function confirms the fact of a linear relation between the laser current and frequency of the generated light with a tuning coefficient of $$0.01 \frac{cm^{-1}}{mA}.$$

Figure 10:
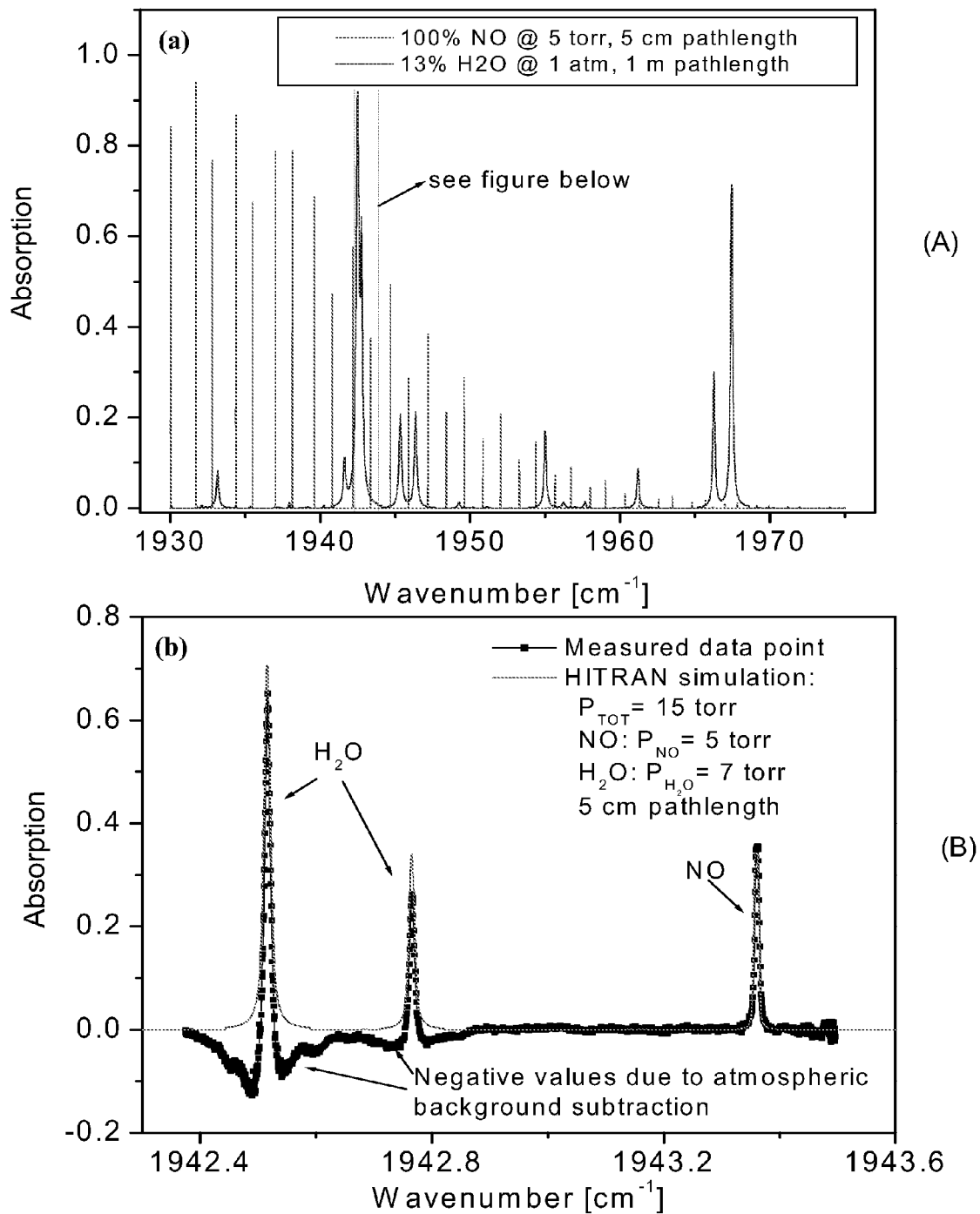
FIG. 10A is a simulated spectra of pure NO at 5 torr in 5 cm reference cell and ambient $H_2O$ absorbing in 1 m open path of the laser beam and FIG. 10B is a single spectral scan of NO and strong neighboring $H_2O$ lines made using a laser constructed in accordance with the present invention.

The tuning range of the present EC-QCL includes several strong water absorption lines. This is illustrated in FIG. 10A, which shows the spectrum simulated using the HITRAN 2000 database for atmospheric $H_2O$ and 1 m path length (this approximately corresponds to the open beam path in a real system) plotted together with the absorption of pure NO at 5 torr and a 5 cm pathlength. The plot has also a very practical function in EC QCL operation, since it serves as a spectroscopic "ruler," which allows a more precise wavelength measurement than the 1/8 wavelength monochromator used in the system (FIG. 1). To demonstrate the capability of multi-species concentration measurements within a single scan, a reference cell, which contained some residual $H_2O$, was evacuated for a short period of time and subsequently filled with pure NO (with a partial pressure of 5 torr). The $H_2O$ absorption lines at 1942.52 $cm^{-1}$ and 1942.76 $cm^{-1}$ were measured along with the NO—R3/2 (21.5) line at 1943.36 $cm^{-1}$. The measured data is plotted in FIG. 10B together with a simulated spectrum. The partial pressure of $H_2O$ was found to be ~7 torr, which is in agreement with the simulation. The background spectrum was measured with the reference cell removed from the optical path. This causes the effective path length in the atmosphere to increase of the reference cell length and results in negative values of the absorption near the low pressure $H_2O$ lines. The negative envelope corresponds to an absorption spectrum of atmospheric $H_2O$ within this additional pathlength. In such a composite plot, the effects of pressure broadening and frequency shift could also be observed.

Theory

The present laser can be analyzed as a system of two coupled cavities: the QCL chip cavity between back and front facet of the QCL and the external cavity that consists of the HR coated back facet and the diffraction grating. The optical length of the QCL cavity is $L_{QCL}=n_{QCL}\times l \approx 1$ cm where $n_{QCL}$ is a refractive index of the chip material and l is its length. The average optical length of the external cavity is ~9.3 cm. This results in free spectral range (FSR) of 0.5 $cm^{-1}$ (15 GHz) and 0.053 $cm^{-1}$ (1.6 GHz) for the QCL and EC Fabry-Perot (FP) resonator, respectively.

The diffraction grating acts as a band pass filter, for which the bandwidth can be estimated by calculating its resolving power $$\Delta\lambda = \frac{\lambda}{|m|N} = \frac{\lambda d \cos\alpha}{a} \quad (1)$$

where $\lambda$ represents the wavelength, m=1 is a diffraction order, a is a diameter of the collimated laser beam and $\alpha$ is the incident angle of the beam measured between the grating normal and the optical axis of the beam. For our system, where $\lambda=5.2$ μm, d=6.67 μm, a=~20 mm and $\alpha=22.95°$ the approximation yields $\Delta\lambda=$~1.6 nm (~0.6 $cm^{-1}$, ~17.7 GHz).

Figure 7:
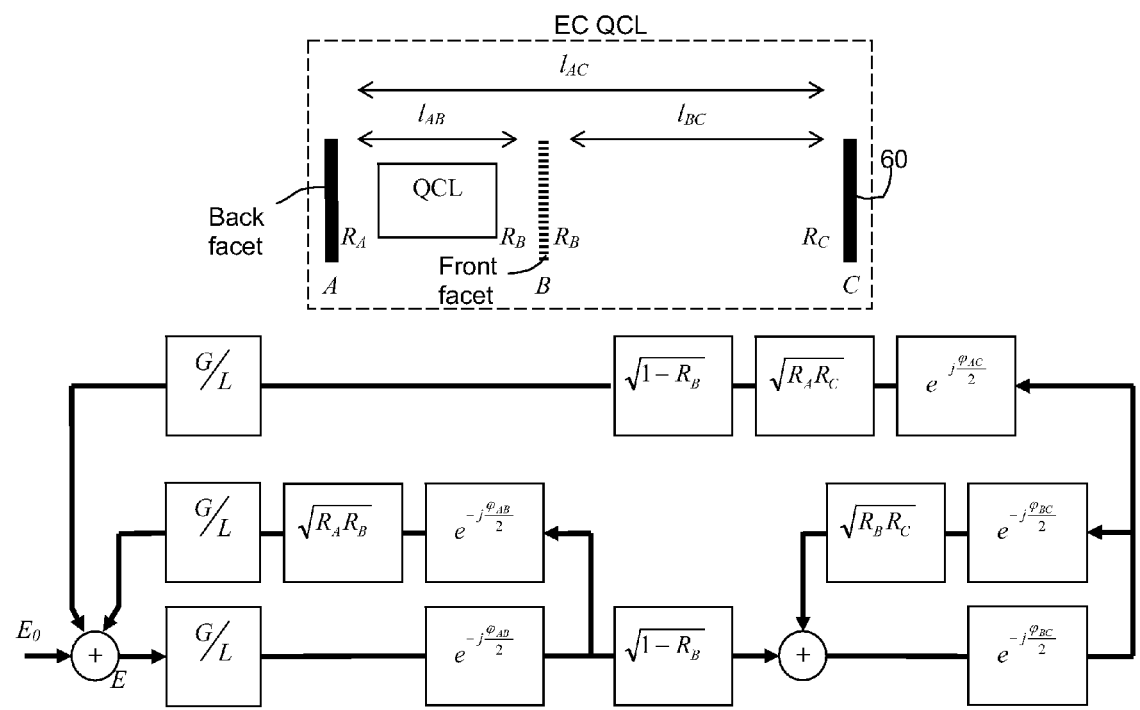
FIG. 7 is a mathematical block diagram modeling an EC laser system with two coupled cavities.

The EC laser behavior during frequency tuning process can be estimated by analyzing an optical system consisting of two coupled optical cavities and the grating filter as discussed above. A mathematical block diagram of such a system is shown in FIG. 7. This yields an expression for the electric field in the QCL FP resonator:

$$E = E_0 \frac{1 - \sqrt{R_B R_C}\, e^{-j\varphi_{BC}}}{1 - \sqrt{R_B R_C}\, e^{-j\varphi_{BC}} - \frac{G}{L}\sqrt{R_A R_B}\, e^{-j\varphi_{AB}} - \frac{G}{L}\sqrt{R_A R_C}\,(1-2R_B)e^{-j\varphi_{AC}}}, \quad \varphi = \frac{4\pi l}{\lambda} \quad (2)$$

where c is velocity of light, $\lambda$ represents the wavelength, $R_A$, $R_B$, $R_C$ are the intensity reflection coefficients (reflectance) of the mirrors, ($\Phi_{AC}$, ($\Phi_{AB}$, ($\Phi_{BC}$ represent the phase shift during a single round trip between mirrors separated by distance l for the following pairs: A and C, A and B, and B and C respectively.

$$G = \exp\left(\frac{1}{2}\gamma(v)l_{QCL}\right)$$

is the single pass gain coefficient and $$L = \exp\left(-\frac{1}{2}\alpha(v)l_{QCL}\right)$$

represents single pass waveguide losses. The presence of the grating can be simulated by substituting a reflectivity of the external mirror by a grating reflectivity function with a peak reflectivity equal to $R_C$. For estimation the collimated laser beam can be approximated by an incident plane wave with intensity $l_1$ illuminating N grooves of the grating. Since the grating does not introduce any phase shift for the incident wave, its wave reflection coefficient $\sqrt{R_{GR}}$ can be calculated using the intensity distribution of light reflected from the diffraction grating, which can be written as $$\sqrt{R_{GR}} = \sqrt{\frac{I_R}{I_I}} = \frac{\sqrt{R_C}}{N}\left|\frac{\sin(N\phi/2)}{\sin(\phi/2)}\right| \quad (3)$$

where $I_R$, is the total reflected intensity of light and $\phi$ is a phase difference between two partial waves reflected by neighboring grooves. For a diffraction grating mounted at an angle $\theta$ using a Littrow configuration, the phase difference can be expressed as $$\phi = \frac{4\pi d}{\lambda}\sin\theta,$$

where d is the distance between two adjacent grooves.

The relative change in the intensity as a function of optical frequency calculated between mirrors A and B (FIG. 7) for a passive QCL FP resonator (assuming that QCL is transparent when G=L) in which all frequency tuning elements (QCL and EC passive FP resonator modes and grating reflectivity spectrum) are centered at the same wavelength is depicted in FIG. 2. The QCL is considered to be a homogenously broadened gain medium as the relaxation processes in semiconductor lasers are fast. However, in the absence of any wavelength selecting element there are modes whose spatial electric field distribution of their standing waves only weakly overlaps the main longitudinal mode. These can simultaneously lase because of spatial hole burning. This is not the case for an EC grating coupled laser, where the separation of the EC FP modes selected by the grating is very small and spatial hole burning can not occur. In such a case, only the strongest of the grating selected longitudinal modes, for which the phase condition is also fulfilled, will lase. In other words, the laser will operate at the frequency of the highest overall peak and nowhere else. Assuming the above, it is possible to simulate the tuning behavior of the laser, which can be done for four different situations:
1) tuning of the effective QCL cavity length while keeping the grating angle and its position with respect to the laser chip constant;
2) simultaneous tuning of both the effective QCL cavity length and EC length while maintaining a constant grating angle;
3) simultaneous tuning of effective QCL cavity length and grating angle while keeping an EC length constant; and
4) simultaneous tuning of all three wavelength selective elements (i.e. effective QCL length, EC length and grating angle).

The results of the simulation, which show fluctuation of the relative intensity and optical frequency of the favorable mode, are shown in FIGS. 3A, B, C, and D, respectively.

In a real system, effective QCL cavity length tuning is accomplished by changing the refractive index of the material through the modulation of the temperature of the active zone, which in turn is generated by the injection current. The optical frequency tuning of the present laser chip FP resonator measured when the QCL was operated in the middle of the gain curve (at ~5.11 µm) and at an injection current of 650 mA, was found to be linear with a rate of $$\frac{dv}{dI} \cong 0.01 \; \frac{cm^{-1}}{mA}.$$

This value was used in the simulation. Since the QCL chip is also a part of the EC, the tuning rate of the EC FP modes at this wavelength should show a tuning rate of the order of:

$$\left(\frac{dv}{dI}\right)_{EC} = \frac{\left(\frac{dv}{dI}\right)_{QCL}}{1 + \frac{l_{EC}}{l_{QCL}}} \approx 0.097 \left(\frac{dv}{dI}\right)_{QCL} \quad (4)$$

This gives a value of $$\sim 9.7 \times 10^{-4} \; \frac{cm^{-1}}{mA}.$$

However in a double cavity system these two comb filters interact with each other, causing a frequency pulling effect. Due to this effect the tuning rate observed for a selected mode in a double cavity system will show a somewhat higher tuning rate than the one calculated for EC only using Eq. 4 This is demonstrated in FIG. 3A, where the frequency tuning rate of the laser selected mode in the simulated system without any mode tracking is $$\sim 0.00135 \frac{cm^{-1}}{mA},$$

which for the simulated conditions is ~40% higher than the value given by Eq. 4. The overall trend observed for the wavelength tuning between two successive QCL FP resonator mode hops is also affected by this phenomena due to the interaction with the grating spectral reflectance function and as a result shows a lower wavelength tuning rate of $$0.0093 \frac{cm^{-1}}{mA}$$

than the one expected for the QCL FP modes. For the system with enabled mode tracking by the EC, whose length is adjusted to equalize wavelength tuning rates for both QCL FP resonator modes and EC FP resonator modes, the tuning rate of the selected laser mode is equal to the applied $$\left(\frac{dv}{dI}\right)_{QCL} = 0.01 \frac{cm^{-1}}{mA}.$$

This can be observed for both mode tracking simulations presented in FIGS. 3B and 3D. In FIG. 3B it is apparent that without appropriate adjustment of the grating angle, mode hops will occur and mode hops between adjacent QCL FP modes can be clearly observed. However, for certain specific configurations of the three element wavelength selective filter (two cavities and the grating) mode-hopping can also occur between two neighboring EC FP resonator modes. This effect is also visible in FIG. 3B.

In a situation when only the grating angle is adjusted to track the laser frequency mode hopping on the EC FP resonator modes will be observed. This is shown in FIG. 3C. By analogy to the simulation in FIG. 3A, the wavelength tuning rate between the mode hops is $$\sim 0.00135 \frac{cm^{-1}}{mA}.$$

However, application of the grating angle tracking caused the overall trend observed for the wavelength tuning to match the initial value of $$0.01 \frac{cm^{-1}}{mA}.$$

In all cases where mode hops occur, a rapid wavelength change is accompanied by modulation of the overall losses within the resonator, which can be observed as changes in the relative intensity plotted in FIGS. 3A-C. This also indicates that the modulation of an intensity of generated light by the active laser will be observed. However for precise analysis of the laser power behavior, which is not a goal of the present work, linear as well as non-linear processes associated with the laser amplification should be taken into account.

As will be understood, the present invention provides a mode-hop free, widely tunable, continuous wave and thermoelectrically cooled EC-QCL capable of performing high resolution spectroscopic measurements. The novel mode frequency tracking system is flexible and can be applied to any other gain media, in particular to those designed for shorter or longer wavelengths, without modification of its mechanical construction. The system ensures independent wavelength tracking by all three wavelength-selective elements of the set-up (QCL cavity, EC and diffraction grating), which makes it suitable for applications employing gain chips even with low efficiency AR coatings on the output facet. The overall spectrometer system performance was demonstrated by means of direct absorption spectroscopic measurements of NO and $H_2O$ at reduced pressures. The present device demonstrates the excellent suitability to perform spectroscopic trace gas concentration measurements using wavelength modulation techniques that offer very high precision. This capability in addition to the wide tunability and high spectral resolution makes the present EC QCL an excellent light source for a number of mid-IR spectroscopic applications such as trace gas detection.

While preferred embodiments of this invention have been shown and described, modifications thereof can be made by one skilled in the art without departing from the scope of this invention. The embodiments described herein are exemplary only and are not limiting. For example, while the components of the present system are moved and controlled using piezo actuators, it will be understood that any device or mechanism capable of providing the desired degree of control could be used instead, including but not limited to electromagnetic actuators or other electromechanical transducers. Likewise, unless explicitly stated otherwise, the sequential recitation of steps in the claims is not intended to require that the steps be performed sequentially, or that a particular step be concluded before another step is commence. Accordingly, the scope of protection is not limited to the embodiments described herein, but is only limited by the claims that follow, the scope of which shall include all equivalents of the subject matter of the claims.

What is claimed is:

1. A mid-IR laser, comprising:
   a laser chip defining an internal cavity and having an effective QCL cavity length;
   a diffraction grating defining a grating angle and an external cavity length with respect to said chip;
   a mirror;
   a first control means for simultaneously controlling the QCL cavity length and a QCL gain, wherein said means for simultaneously controlling the QCL cavity length and the QCL gain consists essentially of varying a single current input to the chip;
   a second control means for controlling the external cavity length without changing the angle of the diffraction grating relative to the laser chip, wherein the second control means comprises a first piezoelectric means; and
   a third control means for simultaneously controlling the diffraction grating and the mirror, wherein the third control means comprises a second piezoelectric means.

2. The laser of claim 1 wherein said chip emits light having wavelengths in the range of 3-30 μm.

3. The laser of claim 1 wherein said chip includes no anti-reflective coating.

4. The laser of claim 1 wherein said chip includes an anti-reflective coating that has a reflectance greater than 0.5%.

5. The laser of claim 1 wherein said second piezoelectric means comprises a piezo-actuated platform that is pivotable relative to said chip without substantially changing the external cavity length, wherein said diffraction grating and said mirror are mounted on said platform.

6. The laser of claim 5 wherein said first piezoelectric means comprises said piezo-actuated platform, wherein said piezo-actuated platform translates linearly relative to said chip.

7. The laser of claim 1 wherein said third control means further comprises a motorized coarse angle control, wherein said first piezoelectric means is a fine external cavity length control, wherein said second piezoelectric means is a fine angle control, and wherein said laser tunes in a mode-hop free manner.

8. The laser of claim 1 wherein the second control means translates the diffracting grating along an axis inline with a QCL cavity, wherein the diffraction grating is oriented along a plane that is not perpendicular to the axis, and wherein the laser chip and the diffraction grating are arranged in a Littrow configuration.

9. A device suitable for high resolution spectroscopic applications and multi species trace-gas detection that includes the laser of claim 1.

10. A method for operating a mid-JR laser so as to avoid mode-hopping, comprising:
    a) providing a laser chip that defines an internal cavity and has an effective QCL cavity length;
    b) providing a diffraction grating that defines a grating angle and an external cavity length with respect to said chip;
    c) supplying power to said chip so that it amplifies electromagnetic radiation within defined gain curve comprising a range of wavelengths; and
    d) automatically and simultaneously controlling the effective QCL cavity length and a QCL gain using a first actuator, the external cavity length using a second actuator, and the diffraction grating using a third actuator such that the laser frequency can be tuned through wavelengths under the gain curve without mode-hopping,
    wherein simultaneously controlling the effective QCL cavity length and the QCL gain using a first actuator consists essentially of varying only one current input to the chip,
    wherein controlling the external cavity length using the second actuator comprises translating the diffraction grating along an axis without pivoting the diffraction grating relative to the chip, wherein the axis is inline with a QCL cavity, and
    wherein the diffraction grating is oriented along a plane that is not perpendicular to the first axis.

11. The method of claim 10 wherein said chip emits light having wavelengths in the range of 3-30 μm.

12. The method of claim 10 wherein said chip includes no anti-reflective coating.

13. The method of claim 10 wherein said chip includes an anti-reflective coating that has a reflectance greater than 0.5%.

14. The method of claim 10 wherein controlling the diffraction grating using the third actuator comprises pivoting the diffraction grating without substantially translating the diffraction grating relative to the chip, and wherein the laser chip and the diffraction grating are arranged in a Littrow configuration.

15. The laser of claim 7 wherein said first piezoelectric means has a resolution of about 0.9 nm.

16. The laser of claim 7 wherein said second piezoelectric means has a resolution of 1.4 μrad/unit.

17. An apparatus comprising:
a laser chip configured to emit a mid-JR beam;
a diffraction grating positioned inline with the beam, wherein the diffraction grating and a back facet of the laser chip define an external cavity having an external cavity length; and
a mirror positioned to receive at least part of the beam from the diffraction grating,
wherein the diffraction grating is configured to move toward or away from the laser chip along a first axis to adjust the external cavity length without changing a diffraction grating angle relative to the beam
wherein the first axis is inline with the beam, and
wherein the diffraction grating is configured to rotate about a second axis orthogonal to the beam without substantially changing the external cavity length.

18. The apparatus of claim 17, wherein the laser chip comprises only one current input, wherein the second axis is inline with the beam, wherein the diffraction grating is oriented along a plane that is not perpendicular to the first axis, and wherein the mirror is not positioned within the external cavity.

19. The apparatus of claim 18 further comprising a simultaneous QCL cavity length and QCL gain controller that consists essentially of a single current input to the chip, wherein the diffraction grating is configured to move toward or away from the laser chip in both an alignment mode that provides beam alignment and a tuning mode that provides mode-hop free tuning, and wherein the diffraction grating is configured to rotate about the axis in both the alignment mode and the tuning mode.

* * * * *